United States Patent
Haddad et al.

[11] Patent Number: 6,054,032
[45] Date of Patent: Apr. 25, 2000

[54] CAPILLARY ELECTROPHORESIS ARRAY

[75] Inventors: Louis C. Haddad, Mendota Heights; Nicholas A. Lee, Woodbury, both of Minn.

[73] Assignee: 3M Innovative Properties Company, St. Paul, Minn.

[21] Appl. No.: 09/013,817

[22] Filed: Jan. 27, 1998

[51] Int. Cl.[7] .......................... G01N 27/26; G01N 27/447
[52] U.S. Cl. ............................................. 204/451; 204/601
[58] Field of Search .................................. 204/451, 452, 204/453, 454, 455, 601, 602, 603, 604, 605; 318/108, 112; 422/58, 104, 103, 54

[56] References Cited

U.S. PATENT DOCUMENTS

| | | | |
|---|---|---|---|
| 4,680,201 | 7/1987 | Hjerten | 204/605 X |
| 4,898,658 | 2/1990 | Karger et al. | 204/605 X |
| 5,268,080 | 12/1993 | Kambara et al. | 204/182.8 |
| 5,277,780 | 1/1994 | Kambara | 204/299 R |
| 5,314,602 | 5/1994 | Kambara et al. | 204/299 R |
| 5,338,427 | 8/1994 | Shartle et al. | 204/604 |
| 5,356,525 | 10/1994 | Goodale et al. | 204/602 |
| 5,366,608 | 11/1994 | Kambara | 204/299 R |
| 5,413,686 | 5/1995 | Klein et al. | 204/603 |
| 5,417,925 | 5/1995 | Goodale et al. | 204/452 |
| 5,434,664 | 7/1995 | Sapp | 356/244 |
| 5,439,578 | 8/1995 | Dovichi et al. | 204/603 |
| 5,529,679 | 6/1996 | Takahashi et al. | 204/603 |
| 5,567,294 | 10/1996 | Dovichi et al. | 204/603 |
| 5,574,817 | 11/1996 | Henson et al. | 385/114 |
| 5,582,705 | 12/1996 | Yeung et al. | 204/603 |
| 5,584,982 | 12/1996 | Dovichi et al. | 204/603 |
| 5,605,666 | 2/1997 | Goodale et al. | 204/603 X |
| 5,611,017 | 3/1997 | Lee et al. | 385/114 |
| 5,695,626 | 12/1997 | Yeung et al. | 204/605 |
| 5,730,850 | 3/1998 | Kambara et al. | 204/603 |
| 5,759,374 | 6/1998 | Takahashi et al. | 204/603 |
| 5,833,827 | 11/1998 | Anazawa et al. | 204/603 |

FOREIGN PATENT DOCUMENTS

| | | |
|---|---|---|
| 0 723 149 A2 | 7/1996 | European Pat. Off. . |
| 0 823 149 A2 | 7/1996 | European Pat. Off. . |
| 42 30 354 A1 | 3/1993 | Germany . |
| WO 94/29712 | 12/1994 | WIPO . |
| WO 94/29713 | 12/1994 | WIPO . |

OTHER PUBLICATIONS

Article: Huang et al., "Capillary Array Electrophoresis Using Laser–Excited Confocal Fluorescence Detection," *Analytical Chemistry*, vol. 64, No. 8, Apr. 15, 1992, pp. 967–972.

*Primary Examiner*—Jill Warden
*Assistant Examiner*—John S. Starsiak, Jr.
*Attorney, Agent, or Firm*—James A. Rogers

[57] ABSTRACT

A capillary electrophoresis array that includes: (a) a plurality of capillary tubes arranged adjacent each other in a generally longitudinal orientation, each of the tubes having an inlet end, and outlet end, and an internal diameter no greater than about 1000 microns; and (b) a registration assembly in which adjacent tubes are held in place with a fixed lateral spacing relative to each other at both the inlet and the outlet ends of the tubes. The array is flexible along the lengths of the tubes.

30 Claims, 6 Drawing Sheets

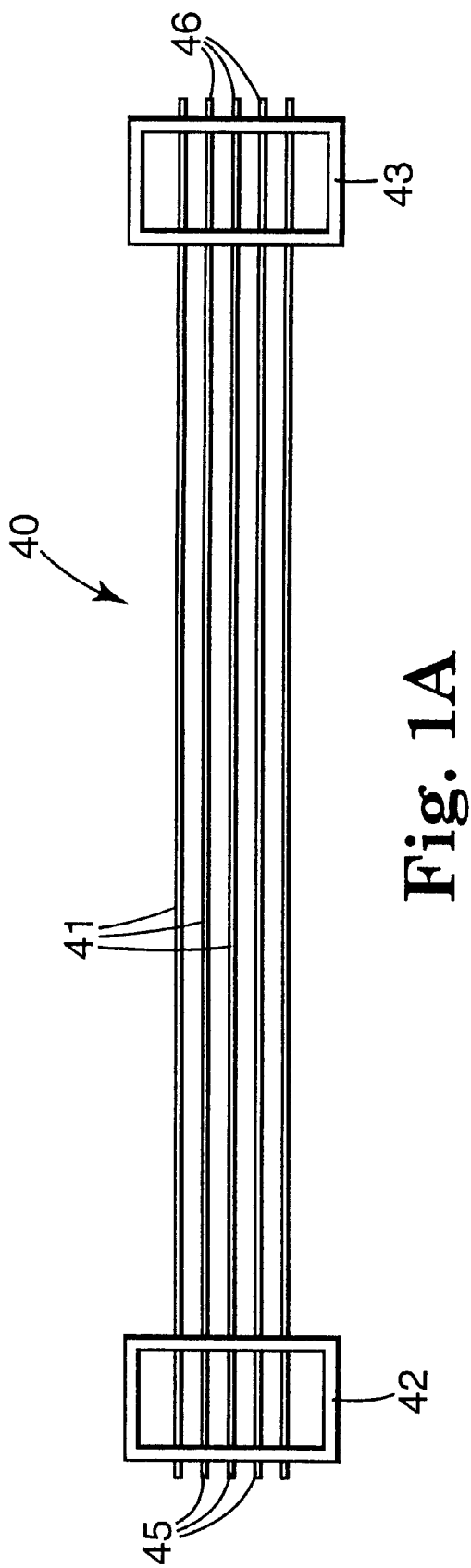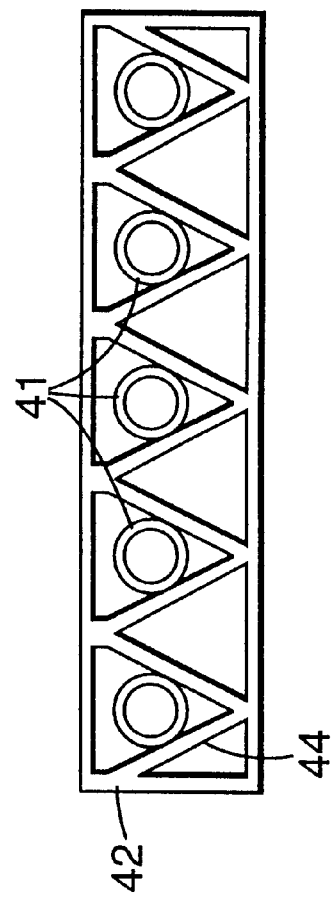
Fig. 1A
Fig. 1B

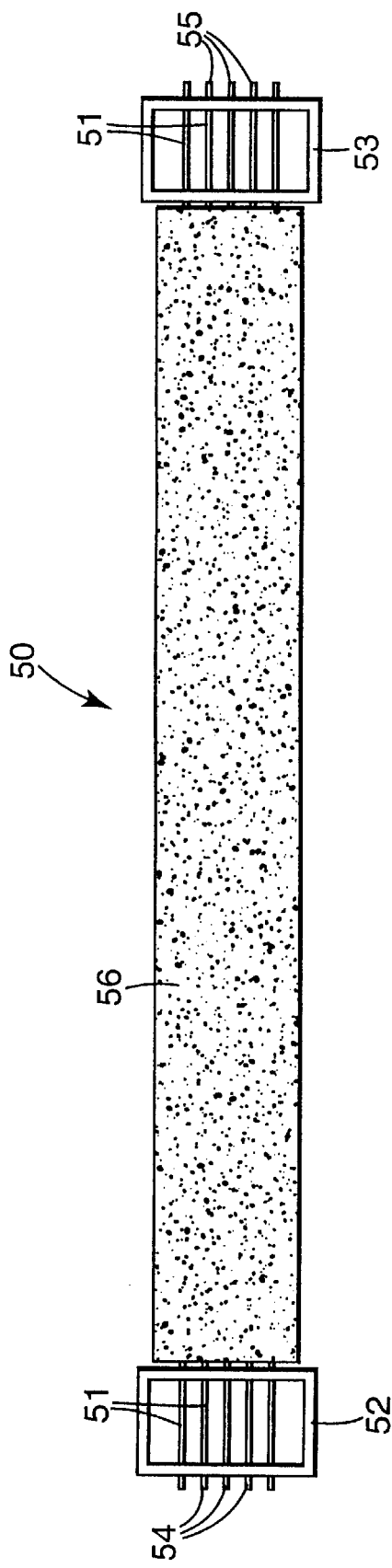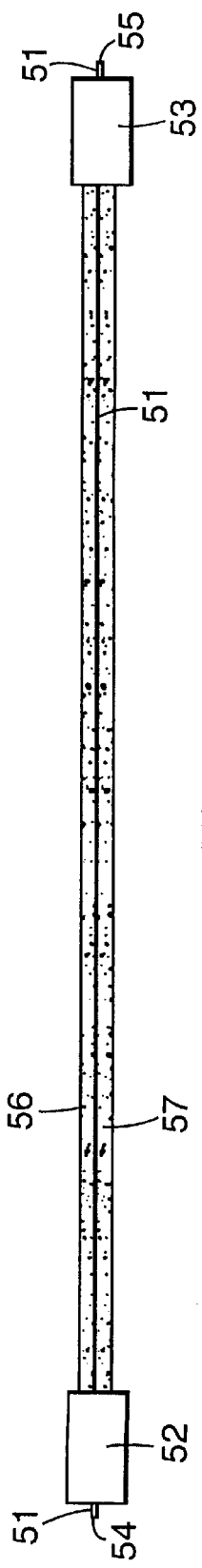

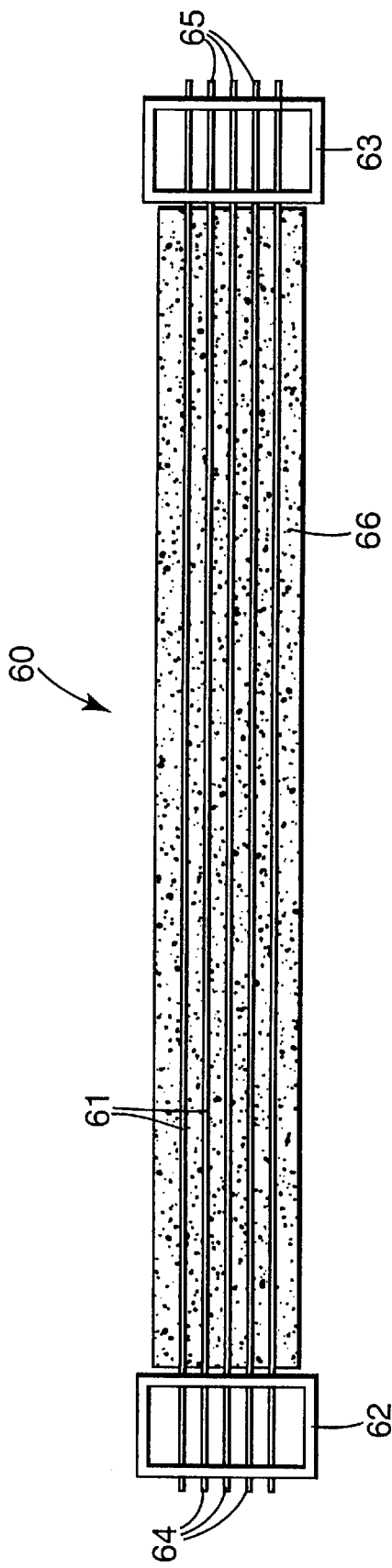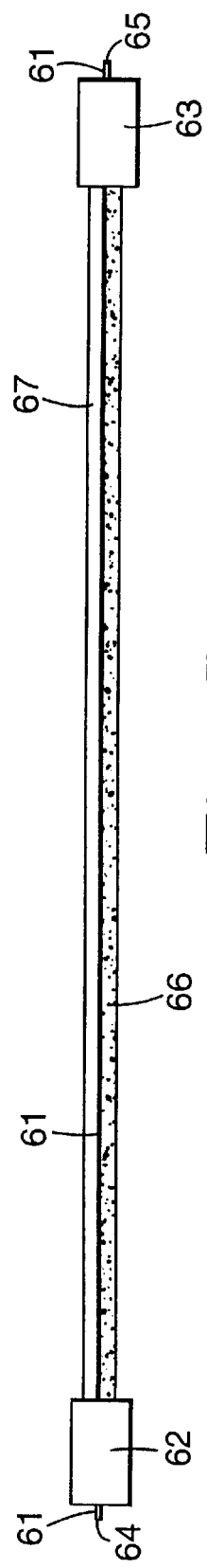
Fig. 3A
Fig. 3B

CAPILLARY ELECTROPHORESIS ARRAY

FIELD

This invention relates to capillary electrophoresis and more specifically to capillary electrophoresis arrays and methods of manufacture and use.

BACKGROUND

Electrophoresis is a technique for separating the charged components of a single or multi-component solution by utilizing differences in the rates of migrations of the charged components in an electric field. The mobility of each charged component, which is equal to the migration rate divided by the field strength, is roughly proportional to its charge to mass ratio. If electrophoresis is performed in a porous medium such as a gel, where molecular sieving takes place, the mobility is also a function of size.

Electrophoresis is a useful tool for separating biological materials such as proteins and nucleic acids. It is particularly useful for nucleic acid sequencing.

Traditionally, electrophoretic separation of biological materials was performed using slabs of gelled materials such as crosslinked polyacrylamide. More recently, electrophoretic separations using very small bore capillary tubes have become popular. This technique requires only very small amounts of samples, and provides high resolution and faster throughput per individual sample than gels.

Capillary electrophoresis is generally performed using fused silica capillary tubes. The tubes may have inner diameters in the range of about 20 to 1000 microns, although typically the inner diameters are no greater than about 100 microns. The tube is coated on its outer surface along its length with an opaque polyimide coating to prevent breakage. In some cases, the separation is performed by filling the capillary tube with only a buffer solution, while in other cases a viscous polymer or gel is added to improve the separation. In general, a sample is introduced into the inlet end of the capillary tube and an electric field applied. Under the influence of the electric field, the sample separates, causing the individual components to migrate down the length of the capillary tube. At the outlet end of the capillary tube, a small region of the opaque polyimide coating is removed to form an optical detection region. The individual components are then detected using, for example, fluorescence or ultraviolet absorbance. Once the polyimide coating has been removed, it is necessary to protect the detection region carefully because the tube is very fragile in the absence of the coating.

Capillary electrophoresis instruments generally employ a single capillary tube and run multiple samples in series. Such an arrangement is not conducive to high throughput screening and nucleic acid sequencing, which would require arrays of capillary tubes for simultaneous analysis of many samples. Such arrays require a means for aligning the tubes precisely and reproducibly so that the inlet and outlet end of each tube can be readily associated with each other, an objective made difficult by the small size and flexibility of the individual tubes. While theoretically each tube could be aligned individually, such an approach would be tedious and time-consuming.

SUMMARY

In a first aspect, the invention features a capillary electrophoresis array that includes: (a) a plurality of capillary tubes arranged adjacent each other in a generally longitudinal orientation, each of the tubes having an inlet end, an outlet end, and an internal diameter no greater than about 1000 microns; and (b) a registration assembly in which adjacent tubes are held in place with a fixed lateral spacing relative to each other at both the inlet and the outlet ends of the tubes. The array is flexible along the lengths of the tubes.

By "fixed lateral spacing" it is meant that, once selected, the lateral spacing between adjacent fibers is held constant. It includes arrays in which the particular spacing between pairs of adjacent tubes is selected such that the spacing may vary from tube to tube and arrays in which the inter-tube spacing is selected such that the spacing is the same throughout the array.

The internal diameter of the tubes is preferably less than about 100 microns. The number of tubes in any one array may vary. In general, however, the array includes at least 5 tubes and, more preferably, at least 25 tubes.

The registration assembly may be configured to hold adjacent tubes in place with a fixed lateral spacing relative to each other substantially along the length of each tube. It may also be configured to maintain the fixed lateral spacing along only a portion of each tube, e.g., at the inlet and outlet ends of the tubes, while allowing the lateral spacing between tubes to vary along the mid-section of the tubes.

In one embodiment, the registration assembly includes a first portion located substantially at the inlet ends of the tubes and a second portion, separate from the first portion, located substantially at the outlet ends of the tubes. For example, each of the portions may include a mechanical fastener, e.g., a block, having a plurality of adjacent grooves with a fixed lateral spacing relative to each other into which the tubes are inserted.

In another embodiment, the registration assembly includes an adhesive tape layer on which the tubes are disposed, or a pair of tape layers between which the tubes are disposed. The tape layer(s) may extend substantially along the length of each tube. Where a pair of adhesive tape layers are employed, one or both of the tape layers may be optically transparent to facilitate detection substantially along the length of each tube.

In yet another embodiment, the registration assembly includes (a) a first portion located substantially at the inlet ends of the tubes and a second portion, separate from the first portion, located substantially at the outlet ends of the tubes, and (b) either an adhesive tape layer on which the tubes are disposed or a pair of adhesive tape layers between which the tubes are disposed. The tape layer(s) may extend substantially along the length of each tube. Where a pair of adhesive tape layers are employed, one or both of the tape layers may be optically transparent to facilitate detection substantially along the length of each tube.

To facilitate detection, the tubes are preferably optically transparent. Preferably, the tubes are optically transparent substantially along the length of each tube, although for some applications it is sufficient that the tubes be optically transparent along only a portion of the length of each tube.

The registration assembly may be configured to perform the additional function of connecting the inlet ends of the tubes to a sample holder.

The array may further include an electrolytic medium disposed within the tubes. Examples of suitable media include buffer solutions and polymer gels. For some applications, it is preferred that the tubes have an internal surface that alters electrophoretic performance relative to the tube in the absence of such an internal surface.

In a second aspect, the invention features a capillary electrophoresis array that includes: (a) a plurality of capillary tubes arranged adjacent each other in a generally longitudinal orientation, each of the tubes having an inlet end and an outlet end; (b) an electrolytic medium disposed within the tubes; and (c) a registration assembly in which adjacent tubes are held in place with a fixed lateral spacing relative to each other at both the inlet and the outlet ends of the tubes. The array is flexible along the lengths of the tubes. Preferably, each of the tubes has an internal diameter no greater than about 1000 microns.

In a third aspect, the invention features a method of conducting electrophoresis that includes: (a) introducing a plurality of samples into a capillary electrophoresis array that includes: (i) a plurality of capillary tubes arranged adjacent each other in a generally longitudinal orientation, each of the tubes having an inlet end and an outlet end; (ii) an electrolytic medium disposed within the tubes; and (iii) a registration assembly in which adjacent tubes are held in place with a fixed lateral spacing relative to each other at both the inlet and the outlet ends of the tubes; and (b) exposing the samples in the tubes to an electric field. The array is flexible along the lengths of the tubes. Each of the samples is introduced into the inlet end of a tube in the array such that each sample occupies a different tube. Each of the tubes preferably has an internal diameter no greater than about 1000 microns. Each of the samples may be introduced into the tubes substantially simultaneously or in series.

In a fourth aspect, the invention features a method of manufacturing a capillary electrophoresis array that includes: (a) orienting a plurality of capillary tubes in a generally longitudinal orientation, each of the tubes having an inlet end and an outlet end; and (b) combining the tubes with a registration assembly to hold adjacent tubes in place with a fixed lateral spacing relative to each other at both the inlet and the outlet ends of the tubes. The array is flexible along the lengths of the tubes.

The invention provides a capillary tube array that aligns multiple capillary tubes precisely and reproducibly so that the inlet and outlet end of each tube are clearly associated with each other. With such arrays, the user can analyze multiple samples quickly and accurately, thereby permitting high throughput screening and nucleic acid sequencing. For example, it is possible to fabricate an array of 96 or more capillary tubes that can simultaneously accept samples from all 96 wells of a standard microwell plate.

Because the arrays are flexible along the lengths of the tubes, they are easy to store, transport, and handle. For example, the arrays are readily connected to a sample holder and/or detector, and then removed when desired. These tubes are also less susceptible to breakage when compared to less flexible tubes. In addition, the number of tubes within the array is not limited. Thus, for example, it is possible to prepare a single array that includes hundreds of tubes. Alternatively, it is possible to achieve the same sample capacity by preparing multiple arrays, each having a smaller number of tubes, in the form of removable modules.

The arrays are manufactured in a process that lends itself to large-scale commercial production. Accordingly, the arrays can be manufactured economically and efficiently. This feature is particularly important in the case of single-use disposable tubes where cost is a factor.

Other features and advantages of the invention will be apparent from the following description of the preferred embodiments thereof, and from the claims.

BRIEF DESCRIPTION OF THE DRAWINGS

FIG. 1A is a top view of a capillary electrophoresis array according to the invention in which a registration assembly includes mechanical fasteners in the form of end blocks.

FIG. 1B is an end view of the capillary electrophoresis array of FIG. 1A.

FIG. 2A is a top view of a capillary electrophoresis array according to the invention in which a registration assembly includes an adhesive tape layer on the top and bottom of the array.

FIG. 2B is a side view of the capillary electrophoresis array of FIG. 2A.

FIG. 3A is a top view of a capillary electrophoresis array according to the invention in which a registration assembly includes a clear adhesive tape layer on the top of the array to allow continuous detection along the entire length of the array.

FIG. 3B is a side view of the capillary electrophoresis array of FIG. 3A.

DETAILED DESCRIPTION

Figure 4:
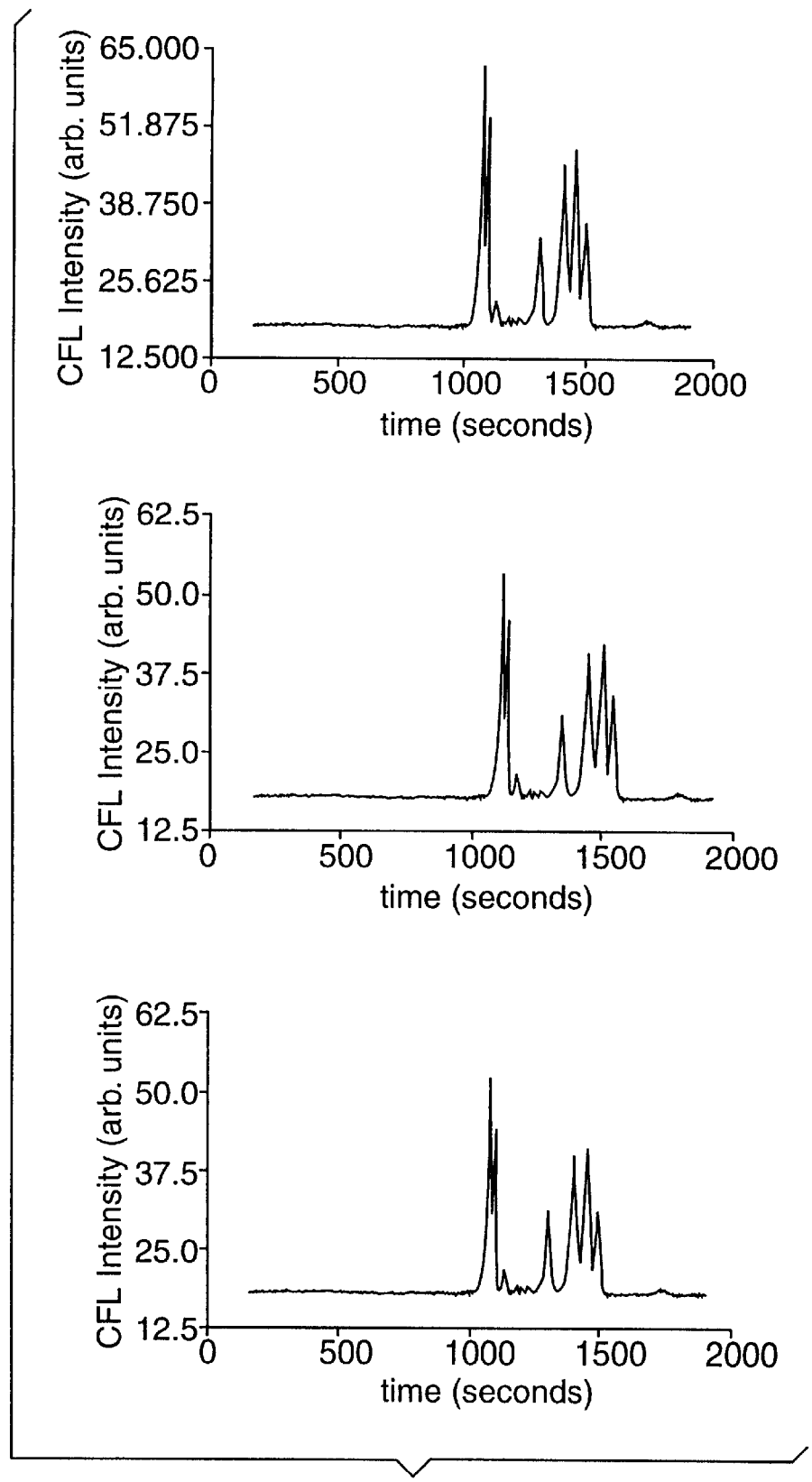
FIG. 4 is a series of electrophoretograms obtained by using a capillary electrophoresis array according to the invention to separate a group of fluorescein-labelled amino acids.

This invention provides capillary electrophoresis arrays in which a plurality of adjacent capillary tubes are held in place with fixed lateral spacing relative to each other at both inlet and outlet ends of the tubes. The array is flexible along the lengths of the tubes.

Referring to FIG. 1A, a capillary electrophoresis array 40 according to the invention is shown. The array includes a plurality of capillary tubes 41 adjacent each other in a generally longitudinal orientation. Each of the tubes has an inlet end 45 and an outlet end 46.

The number of capillary tubes in the capillary electrophoresis array may vary over a wide range. In one preferred embodiment, an array includes at least 5 tubes. In another embodiment, an array includes at least 25 tubes. It will be understood that the number of capillary tubes in the array can vary into ranges of tens, hundreds, or even thousands of tubes. In addition, the number of tubes in a capillary electrophoresis array may be selected to correspond to a number of sample wells, reservoirs, or inputs in instrumentation used in an analytical protocol. For example, the capillary electrophoresis array can include ninety-six tubes to correspond to the number of wells in a standard microwell plate.

The capillary tubes utilized in the arrays typically are of the fused silica type well known in the art. The capillary tubes may have internal diameters of no greater than about 1000 microns, more preferably no greater than about 500 microns. Preferably the internal tube diameters are no greater than about 100 microns. The capillary tubes may optionally include an internal surface that alters electrophoretic performance. Such internal surfaces are known in the art, and typically include a polymer coating that imparts neutral charge to the internal surface. Preferably, the capillary tubes are optically transparent, either in a portion of the tube or, more preferably, over the entire length of the tube. Using tubes that are optically transparent over the entire length of the tube makes it possible to read down the entire length of the tube during sample analysis.

The capillary electrophoresis arrays feature a registration assembly in which adjacent tubes are held in place with a fixed lateral spacing relative to each other at both the inlet and the outlet ends of the tubes. The registration assembly aligns multiple capillary tubes precisely and reproducibly such that the inlet and outlet ends of the tubes are clearly associated with each other. A wide variety of materials and configurations may be employed to provide the registration assembly. In the capillary electrophoresis array shown in FIG. 1A, a registration assembly includes first and second portions 42 and 43, wherein the first portion 42 is located substantially at the inlet end 45 of the tubes, and the second portion is separate from the first portion and is located substantially at the outlet end 46 of the tubes. In certain preferred embodiments, the registration assembly may be configured to connect the inlets 45 or outlets 46 to another piece of equipment such as a sample holder, dispenser, detector array, or power source.

As shown in FIGS. 1A and 1B, the first and second portions of the registration assembly are mechanical fasteners in the form of blocks, although other types of mechanical fasteners, e.g., hook and loop-type fasteners, may be used as well. FIG. 1B shows an end view of the array of FIG. 1A and illustrates a preferred embodiment of such a block. The first portion 42 is a block having a plurality of grooves 44 (shown here in a preferred, V-groove configuration) with a fixed lateral spacing relative to each other into which the tubes 41 have been inserted. The second portion 43 may preferably have the same or a similar block and groove configuration, with the result that the inlets 45 and outlets 46 of the capillary tubes have fixed lateral spacing relative to each other at both the inlet and outlet ends. The first and second portions of the registration assembly may also be in the form of, for example, a tape layer or a pair of tape layers, glue, polymer coatings, and the like.

In the capillary electrophoresis array illustrated in FIGS. 1A and 1B, where the registration assembly includes first and second portions substantially at the inlet and outlet ends, respectively, of the tubes, the lateral spacing of the segments of the capillary tubes between the first and second portions can vary. This feature may be desirable for some applications. For other applications, it may be desirable to provide a registration assembly that achieves fixed lateral spacing of adjacent capillary tubes relative to each other substantially along the length of each tube. FIGS. 2A–B and 3A–B illustrate embodiments of the capillary electrophoresis array of the invention in which a registration assembly is configured to hold adjacent tubes in place with a fixed lateral spacing relative to each other substantially along the length of each tube.

Referring now to FIG. 2A, a capillary electrophoresis array 50 of the invention is shown in top view. The array includes a plurality of capillaries 51 having inlet ends 54 and outlet ends 55. The registration assembly in the array 50 includes first and second portions 52 and 53, respectively, in similar fashion to the array shown in FIGS. 1A–B. The registration assembly of the array 50 of FIGS. 2A–B additionally includes adhesive tape layers 56 and 57 (layer 57 shown in side view in FIG. 2B), between which capillary tubes 51 are disposed and held in place with fixed lateral spacing relative to each other substantially along the length of each tube. Adhesive tape layers 56 and 57 as shown in FIGS. 2A–B are opaque. If desired, a portion of one, or both, of the layers could be transparent, or removed, to allow detection of the contents of the capillary tubes disposed between the tape layers. Alternatively, the entirety of one, or both, of the tape layers can be optically transparent, as shown in FIGS. 3A–B.

Referring now to FIGS. 3A–B, a capillary electrophoresis array 60 is shown. The array 60 is similar to the array shown in FIGS. 2A–B except that one of the tape cladding layers 67 is optically transparent. The array 60 includes a plurality of capillaries 61 having inlet ends 64 and outlet ends 65. The registration assembly in the array 50 includes first and second portions 62 and 63, respectively, in similar fashion to the array shown in FIGS. 1A–B and 2A–B. The registration assembly of the array 60 of FIGS. 3A–B additionally includes adhesive tape layers 66 and 67 (layer 67 shown in side view in FIG. 2B), which extend substantially along the length of each tube, and of which layer 67 is optically transparent; as noted above, it is also possible to make adhesive tape layer 66 transparent as well. The capillary tubes 61 are disposed and held in place with fixed lateral spacing relative to each other substantially along the length of each tube. The optically transparent layer 67 allows for continuous detection along the entire length of the capillary tube.

In embodiments in which it is desirable to configure the registration assembly to hold adjacent tubes in place with fixed lateral spacing relative to each other substantially along the length of each tube, a variety of materials and configurations can be employed for this purpose. For example, any type of adhesive tape, glue, resin, or the like that is capable of holding the tubes in fixed lateral alignment would be suitable. Optically transparent varieties of these materials can be selected if that feature is desired.

The capillary electrophoresis arrays may be employed in any mode of capillary electrophoresis known in the art, including capillary zone electrophoresis, capillary gel electrophoresis (using cross-linked and uncross-linked gels), and capillary isoelectric focusing. In many applications, such as isoelectric focusing, it is preferred that the tubes (and registration assembly, where the registration assembly includes elements such as adhesive tape layers that extend the length of the tube) be optically transparent along their length so that it is possible to read down the entire length of the tube.

The arrays may also be used in conjunction with any analytical or signal detection protocol, including luminescence detection (e.g, chemiluminescence, fluorescence, phosphorescence), radiochemical detection, mass spectroscopy, and detection by the use of photographic films in conjunction with signal-generating substances. The aforementioned capillary electrophoresis modes and analytical/signal detection protocols all are well known and understood in the art.

The invention also features capillary electrophoresis arrays as described herein in which an electrolytic medium is disposed within the capillary tubes. The electrolytic medium may be selected for a particular capillary electrophoresis protocol, and may include, for example, a buffer solution, a polymer gel, or reagents for setting up a pH gradient along the length of the capillary tubes.

The invention further features a method of conducting electrophoresis using a plurality of samples. The method involves introducing a plurality of samples into a capillary electrophoresis array in accordance with any embodiment of the array as described herein, and exposing the samples in the tubes to an electric field. The samples may be introduced simultaneously or sequentially. After an appropriate time has elapsed, the separated components of the sample in each tube can be detected using methods well known in the art. Advantageously, the method allows for efficient, precise, and high throughput analysis of the multiple samples. By virtue of the registration assembly in the array, the inlet and outlet ends of each capillary tube can be clearly associated with each other, thereby increasing efficiency and accuracy.

Figure 5:
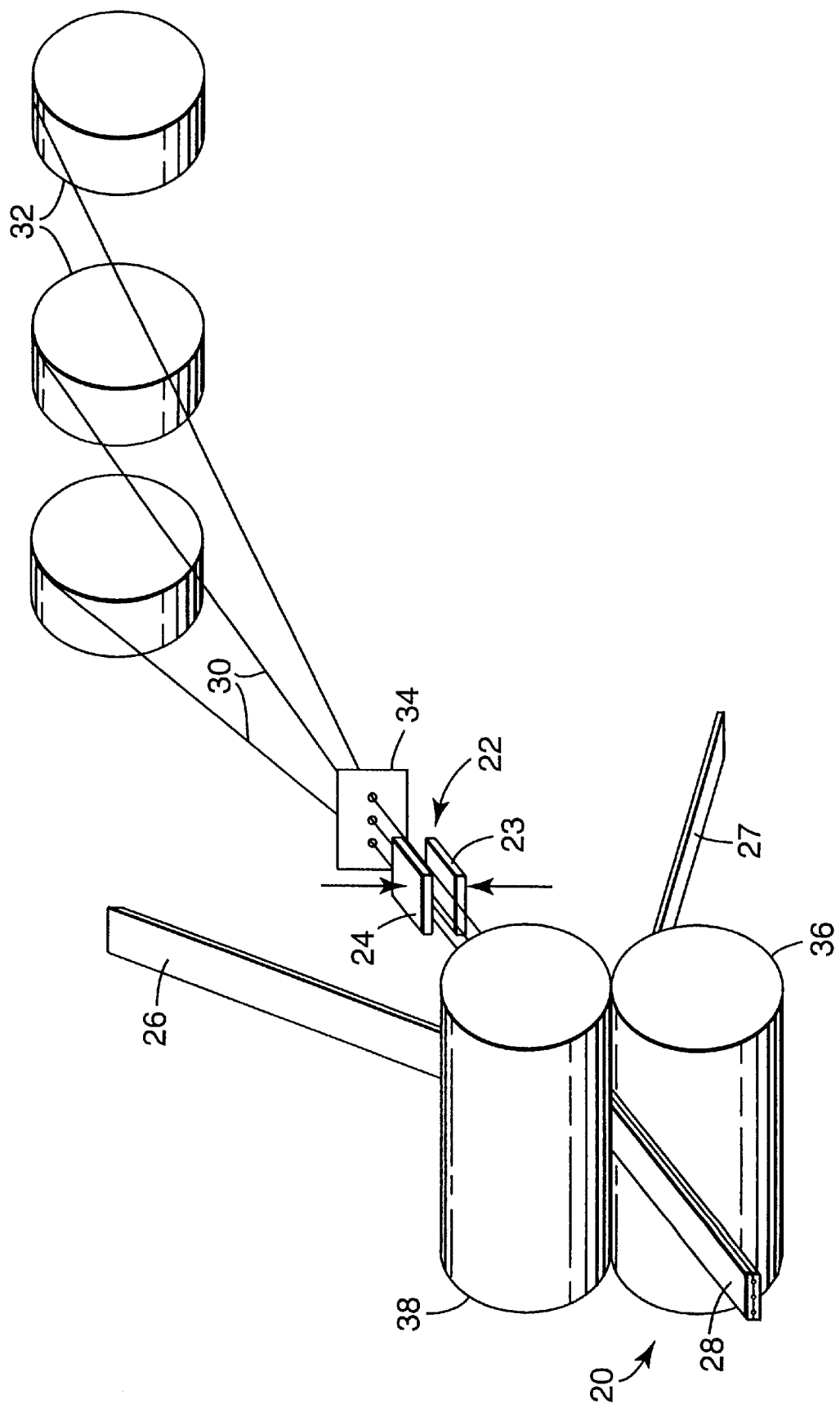
FIG. 5 illustrates a process for manufacturing a capillary electrophoresis array of the invention.
Figure 6:
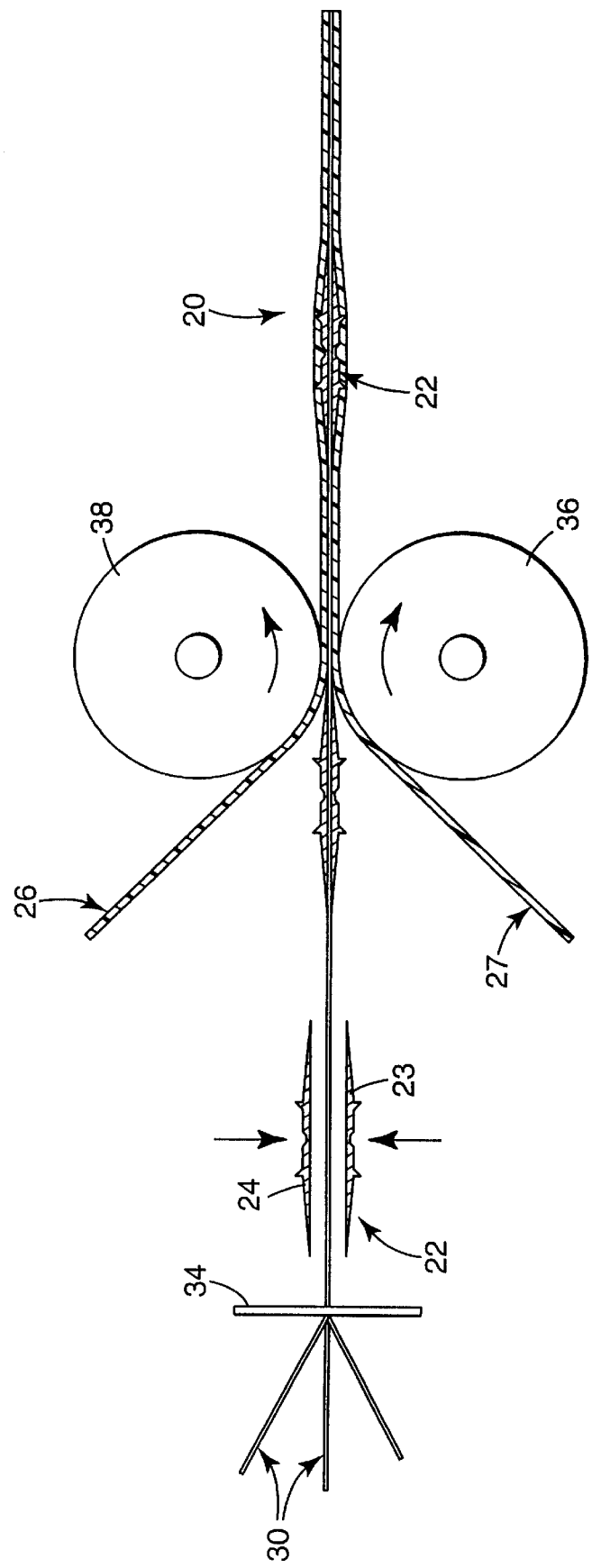
FIG. 6 is a side view of a process for manufacturing a capillary electrophoresis array of the invention.

The capillary tube array is preferably manufactured according to the process generally described in Henson et al., U.S. Pat. No. 5,574,817, which is hereby incorporated by reference, and exemplified in FIGS. 5 and 6. FIGS. 5 and 6 illustrate a process for manufacturing a capillary tube array in which the registration assembly includes a two-component apparatus that sandwiches the capillary tubes at one end in combination with a pair of adhesive tape layers. It will be understood that capillary tube arrays having different registration assemblies may be manufactured by making appropriate modifications to the process illustrated in FIGS. 5 and 6.

Referring to FIG. 5, a plurality of capillary tubes 30 are drawn from a corresponding series of spools 32 through a guiding comb 34. Guiding comb 34 is provided with a structure to establish a fixed, lateral, inter-tube spacing between capillary tubes 30. Preferably, this spacing corresponds with a fixed, lateral, inter-tube spacing of a registration assembly 22 which preferably includes a pair of upper and lower components 23, 24. After capillary tubes 30 are brought through guiding comb 34, registration assembly components 23, 24 are positioned to sandwich capillary tubes 30 therebetween, thereby fixing the lateral inter-tube dimension within registration assembly 22. At a point further downstream in the process, a lower adhesive tape layer 26 and an upper adhesive tape layer 27, which also form part of registration assembly 22, are introduced to sandwich capillary tubes 30 therebetween to create capillary tube array 20. A pair of compression rollers 36, 38 are preferably used to supply the force necessary to secure lower adhesive tape layer 26 to upper adhesive tape layer 27. Rollers 36, 38 also help pull the array down to the point where additional components 23, 24 forming the registration assembly are added.

Referring now to FIG. 6, a side view of the manufacturing process is shown in which it is demonstrated how components 23, 24 are inserted at discrete locations along the longitudinal length of capillary tubes 30 during the manufacturing process. By controlling the positioning and number of components 23, 24, it is possible to produce a continuous run of aligned capillary tubes having a series of segments, each with a length effectively determined by the positioning of sequential component assemblies 23, 24. Individual arrays are then produced by cutting the continuous run in an orientation generally perpendicular to the longitudinal orientation of capillary tubes 30.

The invention will now be described further by way of the following example.

EXAMPLE 1

An electrophoretic separation of a group of amino acids labeled with fluorescein was run using a confocal microscope as a fluorescence detector.

A capillary array device was constructed and consisted of five 70 cm long capillaries made from high purity fused silica. The capillaries had an internal diameter of about 100 microns and external diameter of about 200 microns. During fabrication the capillaries were coated to a final outer diameter of about 300 microns with an optically transparent acrylated urethane coating. The capillaries were held in registration by two V-groove blocks, the first located at the proximal end of the array and the second about 30 cm from the distal end. Each V-groove block consisted of a polymeric base containing a row of 20 V-grooves at a 500 micron pitch and a transparent polymeric cover. The capillaries were aligned within five of the V-grooves in the base and the cover applied and bonded in place to secure the capillaries. Distal to the second V-groove block the capillaries were pushed through a rubber stopper which could be connected to a vacuum flask to aid in flushing and filling. The capillaries at the proximal end were scored and broken so that they were all the same length and extended about 1 cm out from the polymeric base.

This array was used for the experiment below. Similar devices were also prepared with an adhesive tape sheath on one or both sides of the capillaries between the polymeric V-groove blocks. These tape sheaths held the capillaries in parallel registration throughout their entire length. In one array the tape sheath was an optically transparent film which allowed detection to take place anywhere along its length.

Fluorescein labelling of amino acids was done according to the method of Efenhauser, Manz, and Widmer (Analytical Chemistry 65 pp 2637–2642 (1993)). The amino acids, 1-arginine, 1-glutamine, 1-glutamic acid, and 1-phenylalanine, were obtained from Aldrich Chemical Co., Milwaukee, Wis. 53233. Separate 10 mM solutions of each of these were prepared in a pH 9.2 buffer prepared from 20 mM boric acid and 100 mM tris(hydroxymethyl) aminomethane (TRIS). One mL of each of these solutions was mixed with 2 mL of a 1 mM acetone solution of fluorescein isothiocyanate (mixed isomers, Sigma Chemical Co., St. Louis, Mo. 63178) which contained about 0.05% pyridine as a catalyst. This mixture was allowed to react at room temperature overnight, diluted 1:10 with additional buffer and then used without further treatment.

The capillary array device was laid across the stage of a Leica TCS-4D LSCM confocal microscope with all five capillaries held in registration. The microscope's field of view was set at a point that was 28 cm from the sample injection end of the capillaries. Because it was optically transparent it was not necessary to remove the acrylated urethane coating from the capillaries at this detection point. Excitation and fluorescent emission took place right through the coating.

The 488 nm emission from an Argon-Krypton laser was used to excite the sample. Fluorescent emission from the sample was detected through a 525 nm bandpass filter. A 2.5/0.07 NA objective was used to both excite the sample and collect the emission. Images of all five capillaries at this position were collected and digitally stored every 0.31 seconds. The data from these stored images were then used to construct electrophoretograms (fluorescent intensities vs time) for each of the five capillaries.

To conduct the electrophoretic separation, the capillaries were flushed with 1 M sodium hydroxide, followed by water and finally 40 mM borate buffer at pH 9.2. The capillaries were left filled with this buffer which served as the running buffer. Flushing and filling were done with the aid of a vacuum. The five capillaries were simultaneously loaded at one end by vacuum with approximately 150 nanoliters of the above mixture of fluorescein labeled amino acids. This end was immersed in a 30 ml beaker of the running buffer (40 mM borate pH 9.2). A short length of 18 gauge platinum wire was immersed in the buffer in this beaker and connected to the positive side of a 4000 volt constant voltage power supply to serve as the anode. The other end of the capillary array was immersed in a second beaker of the running buffer. A short length of 18 gauge platinum wire in this beaker was connected to the negative side of the power supply.

Immediately after set up, the power supply was turned on (actual measured voltage was 4060 volts) and the fluorescent emission of each of the five capillaries monitored for about 50 minutes. During this time the total current through all five capillaries stayed at around 30 microamps.

Electrophoretograms for each of the five capillaries in the array were constructed from the image data taken through the microscope. The five electrophoretograms were all very similar, indicating that substantially the same separation took place simultaneously in each capillary. The electrophoretograms for three of the capillaries in the array are shown in FIG. 4.

Other embodiments are within the following claims.

What is claimed is:

1. A capillary electrophoresis array comprising:
   (a) a plurality of capillary tubes arranged adjacent each other in a generally longitudinal orientation, each of said tubes having an inlet end, an outlet end, and an internal diameter no greater than about 100 microns; and
   (b) a unitary registration assembly in which adjacent tubes are bonded in place with a fixed lateral spacing relative to each other at both the inlet and the outlet ends of said tubes,
   said array being flexible along the lengths of said tubes.

2. A capillary electrophoresis array according to claim 1 wherein said registration assembly is configured to hold adjacent tubes in place with a fixed lateral spacing relative to each other substantially along the length of each tube.

3. A capillary electrophoresis array according to claim 1 wherein said registration assembly comprises a first portion located substantially at the inlet ends of said tubes and a second portion, separate from said first portion, located substantially at the outlet ends of said tubes.

4. A capillary electrophoresis array according to claim 3 wherein each of said portions comprises a mechanical fastener having a plurality of adjacent grooves with a fixed lateral spacing relative to each other into which said tubes are inserted.

5. A capillary electrophoresis array according to claim 1 wherein said registration assembly is configured to connect the inlet ends of said tubes to a sample holder.

6. A capillary electrophoresis array according to claim 1 wherein said registration assembly comprises an adhesive tape layer on which said tubes are disposed.

7. A capillary electrophoresis array according to claim 6 wherein said adhesive tape layer extends substantially along the length of each tube.

8. A capillary electrophoresis array according to claim 1 wherein said registration assembly comprises a pair of adhesive tape layers between which said tubes are disposed.

9. A capillary electrophoresis array according to claim 8 wherein each of said adhesive tape layers extends substantially along the length of each tube.

10. A capillary electrophoresis array according to claim 1 wherein said registration assembly comprises (a) a first portion located substantially at the inlet ends of said tubes and a second portion, separate from said first portion, located substantially at the outlet ends of said tubes, and (b) an adhesive tape layer on which said tubes are disposed.

11. A capillary electrophoresis array according to claim 10 wherein said adhesive tape layer extends substantially along the length of each tube.

12. A capillary electrophoresis array according to claim 1 wherein said registration assembly comprises (a) a first portion located substantially at the inlet ends of said tubes and a second portion, separate from said first portion, located substantially at the outlet ends of said tubes, and (b) a pair of adhesive tape layers between which said tubes are disposed.

13. A capillary electrophoresis array according to claim 12 wherein each of said adhesive tape layers extends substantially along the length of each tube.

14. A capillary electrophoresis array according to claim 1 wherein said tubes are optically transparent.

15. A capillary electrophoresis array according to claim 4 wherein said tubes are optically transparent substantially along the length of each tube.

16. A capillary electrophoresis array according to claim 1 further comprising an electrolytic medium disposed within said tubes.

17. A capillary electrophoresis array according to claim 16 wherein said electrolytic medium comprises a buffer solution.

18. A capillary electrophoresis array according to claim 16 wherein said electrolytic medium comprises a polymer gel.

19. A capillary electrophoresis array according to claim 1 wherein said tubes have an internal surface that provides material properties which enhance electrophoretic separation performance within said tubes.

20. A capillary electrophoresis array according to claim 1 wherein said array comprises at least 5 tubes.

21. A capillary electrophoresis array according to claim 1 wherein said array comprises at least 25 tubes.

22. A capillary electrophoresis array, comprising:
   (a) a plurality of capillary tubes arranged adjacent each other in a generally longitudinal orientation each of said tubes having an inlet end, an outlet end, and an internal diameter no greater than about 1000 microns; and
   (b) a registration assembly in which adjacent tubes are held in place with a fixed lateral spacing relative to each other at both the inlet and the outlet ends of said tubes, wherein said registration assembly comprises an adhesive tape layer on which said tubes are disposed and wherein said adhesive tape layer is optically transparent,
   said array being flexible along the lengths of said tubes.

23. A capillary electrophoresis array, comprising:
   (a) a plurality of capillary tubes arranged adjacent each other in a generally longitudinal orientation, each of said tubes having an inlet end, an outlet end, and an internal diameter no greater than about 1000 microns; and
   (b) a registration assembly in which adjacent tubes are held in place with a fixed lateral spacing relative to each other at both the inlet and outlet ends of said tubes, wherein said registration assembly comprises a pair of adhesive tape layers between which said tubes are disposed, and wherein at least one of said adhesive tape layers is optically transparent,
   said array being flexible along the lengths of said tubes.

24. A capillary electrophoresis array, comprising:
   (a) a plurality of capillary tubes arranged adjacent each other in a generally longitudinal orientation, each of said tubes having an inlet end, an outlet end, and an internal diameter no greater than about 1000 microns; and
   (b) a registration assembly in which said adjacent tubes are held in place with a fixed lateral spacing relative to each other at both the inlet and the outlet ends of said tubes, wherein said registration assembly comprises
      (i) a first portion located substantially at the inlet ends of said tubes and a second portion, separate from said first portion, located substantially at the outlet ends of said tubes; and (ii) an adhesive tape layer on which said tubes are disposed, and wherein said adhesive tape layer is optically transparent, said array being flexible along the lengths of said tubes.

25. A capillary electrophoresis array, comprising:
(a) a plurality of capillary tubes arranged adjacent each other in a generally longitudinal orientation, each of said tubes having an inlet end, an outlet end, and an internal diameter no greater than about 1000 microns; and
(b) a registration assembly in which adjacent tubes are held in place with a fixed lateral spacing relative to each other at both the inlet and outlet ends of said tubes, wherein said registration assembly comprises
   (i) a first portion located substantially at the inlet ends of said tubes and a second portion, separate from said first portion, located substantially at the outlet ends of said tubes; and
   (ii) a pair of adhesive tape layers between which said tubes are disposed, wherein at least one of said adhesive tape layers is optically transparent, said array being flexible along the lengths of said tubes.

26. A capillary electrophoresis array comprising:
(a) a plurality of capillary tubes arranged adjacent each other in a generally longitudinal orientation, each of said tubes having an inlet end and an outlet end;
(b) an electrolytic medium disposed within said tubes; and
(c) a unitary registration assembly in which adjacent tubes are bonded in place with a fixed lateral spacing relative to each other at both the inlet and the outlet ends of said tubes, said array being flexible along the lengths of said tubes.

27. A capillary electrophoresis array according to claim 26 wherein each of said tubes has an internal diameter no greater than about 100 microns.

28. A method of conducting electrophoresis comprising:
(a) introducing a plurality of samples into a capillary electrophoresis array comprising:
   (i) a plurality of capillary tubes arranged adjacent each other in a generally longitudinal orientation, each of said tubes having an inlet end and an outlet end;
   (ii) an electrolytic medium disposed within said tubes; and
   (iii) a unitary registration assembly in which adjacent tubes are bonded in place with a fixed lateral spacing relative to each other at both the inlet and the outlet ends of said tubes, said array being flexible along the lengths of said tubes, each of said samples being introduced into the inlet end of a tube in said array such that each sample occupies a different tube; and
(b) exposing said samples in said tubes to an electric field.

29. A method according to claim 28 wherein each of said tubes has an internal diameter no greater than about 100 microns.

30. A method according to claim 28 comprising introducing each of said samples into said tubes substantially simultaneously.

* * * * *